Figure 1:
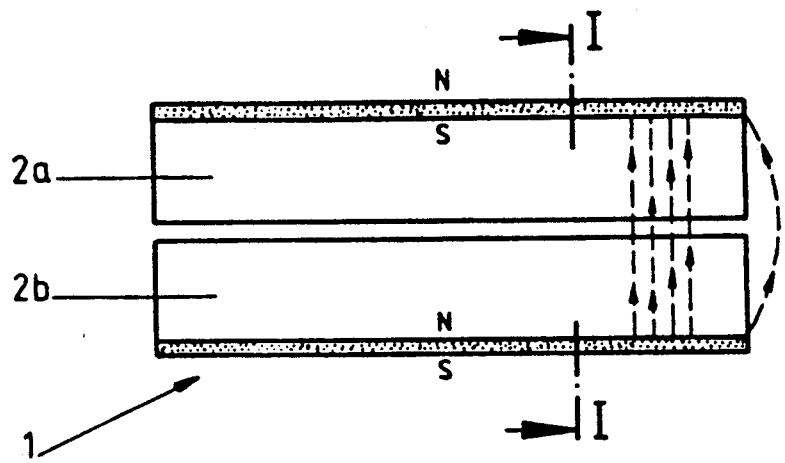

United States Patent [19]

Baermann

[11] Patent Number: 5,017,185

[45] Date of Patent: May 21, 1991

[54] PERMANENT MAGNETIC ARRANGEMENT FOR THERAPEUTIC PURPOSES

[75] Inventor: Horst Baermann, Roesrath, Fed. Rep. of Germany

[73] Assignee: Rheinmagnet, Horst Baermann, GmbH, Neunkirchen, Fed. Rep. of Germany

[21] Appl. No.: 485,753

[22] Filed: Feb. 23, 1990

Related U.S. Application Data

[63] Continuation of Ser. No. 220,406, Jun. 20, 1988, abandoned, which is a continuation of Ser. No. 73,919, Jul. 13, 1987, abandoned, which is a continuation of Ser. No. 845,575, Mar. 28, 1986, abandoned.

[30] Foreign Application Priority Data

Mar. 29, 1985 [DE] Fed. Rep. of Germany ....... 3511395

[51] Int. Cl.$^5$ .............................................. A61N 1/00
[52] U.S. Cl. ..................................................... 600/15
[58] Field of Search ..................... 600/9, 15; 335/302, 335/303, 306

[56] References Cited

U.S. PATENT DOCUMENTS

| | | | |
|---|---|---|---|
| 410,652 | 9/1889 | Scott | 128/1.3 |
| 2,409,866 | 10/1946 | Jewell | 335/306 |
| 2,797,370 | 6/1957 | Bennett | 335/303 |
| 3,005,458 | 10/1961 | Brook et al. | 128/1.3 |
| 3,254,859 | 4/1962 | Reisch | 335/303 |
| 3,921,620 | 11/1975 | Nakayama | 128/1.3 |
| 4,162,672 | 7/1979 | Yazaki | 128/1.3 |
| 4,186,729 | 2/1980 | Harrison | 128/1.3 |
| 4,206,749 | 6/1980 | Bucalo | 128/1 R |
| 4,374,516 | 2/1983 | Harrison | 128/1.3 |
| 4,391,270 | 7/1983 | Uragami | 128/1.3 |
| 4,480,596 | 11/1984 | Shumiyashu | 128/1.3 |
| 4,489,711 | 12/1984 | Latzke | 128/1.3 |

FOREIGN PATENT DOCUMENTS

| | | | |
|---|---|---|---|
| 1464249 | 11/1963 | Fed. Rep. of Germany | 335/302 |
| 2335475 | 1/1975 | Fed. Rep. of Germany | . |
| 2506227 | 8/1976 | Fed. Rep. of Germany | . |
| 3147852 | 4/1983 | Fed. Rep. of Germany | . |
| 3325356 | 7/1983 | Fed. Rep. of Germany | 128/1.3 |
| 56-7405 | 1/1981 | Japan | 117/42 |
| 1665 | 6/1872 | United Kingdom | 128/1.3 |
| 5111 | 10/1883 | United Kingdom | 128/1.3 |

OTHER PUBLICATIONS

*NMR Imaging in Biomedicine,* Mansfield et al., 1982, pp. 297-310.

"The Application of Alternating Magnetic Field in Medicine", Peter Kokoschinegg, Copyright Sep., 1982, pp. 1-12.

*Primary Examiner*—Randall L. Green
*Assistant Examiner*—Randy Shay
*Attorney, Agent, or Firm*—Body, Vickers & Daniels

[57] ABSTRACT

A permanent magnetic arrangement for therapeutic purposes, which comprises one or several rubber-type flexible magnetic foils or strips in which highly coercive permanent magnet particles are embedded in a tube-shape during the therapeutic treatment. The magnetic foils or strips are magnetized perpendicularly to their surface, whereby their magnetic field lines pass through the body section enclosed by the magnetic foil or foil pieces, in cross-wise and/or longitudinal direction. The magnetic foil or foil pieces are positioned in a textile fabric strip, which is provided on its open ends with a fastening mechanism, preferably a Velcro fastener in the form of a bandage. In order to increase the magnetic field line density, the magnetic foils or foil pieces or strips are positioned in layers one over the other, whereby in each case north poles of one foil are opposite south poles of the adjacent foil.

3 Claims, 4 Drawing Sheets

PERMANENT MAGNETIC ARRANGEMENT FOR THERAPEUTIC PURPOSES

This is a continuation of U.S. Ser. No. 220,406 filed June 20, 1988 now abandoned which is a continuation of U.S. Ser. No. 073,919 filed July 13, 1987 now abandoned which is a continuation of U.S. Ser. No. 845,575 filed Nov. 28, 1986 now abandoned.

The invention refers to a permanent magnetic arrangement for therapeutic purposes on the human body, which comprises one or several rubber-type flexible permanent magnetic foils or strips, in which the highly coercive permanent magnetic particles are embedded.

It has already become known that the magnetic fields of such flexible magnetic foils can stimulate blood circulation.

These magnetic foils can either have a pole sequence with alternating polarity on one surface or be provided with an axial magnetization, whereby the north poles are present on one surface and the south poles are present on the opposite surface of the foil. These magnetic foils are applied to the part of the body to be treated in the form of magnetic plasters or, when they have been magnetized perpendicularly to the surface of the foil, placed in cushions or blankets. U.S. Pat. No. 4,549,532.

It has already been discovered, that the healing process in the case of bone fractures is speeded up when an electromagnetically produced alternate field of varying frequency and/or strength is allowed to act on the point of fracture.

In order to produce the alternate field, coils provided with a casing, e.g., in the form of a tunnel, are required, which have such a size or diameter sufficient to completely surround the point of fracture.

These appliances are heavy and permit only stationary use. Furthermore, they are usually of a complicated design, so that production costs are high.

It is the object of this invention to avoid these disadvantages and to create a permanent magnetic arrangement which brings about an improvement in the foregoing areas of therapeutic application at low cost.

This object is achieved according to the invention by a permanent magnetic arrangement in the shape of a flexible tube which surrounds the part of the body needing therapeutic care.

It has been shown, that according to the invention particularly good results are achieved in specific therapeutic applications, such as speeding up the healing process for bone fractures, the results being comparable to those of the therapy with the complicated electromagnetically stimulated coils.

A particularly surprising effect according to the invention obviously seems to be that the part of the body to be treated is enclosed completely by the tube-shaped permanent magnetic arrangement and that according to the suggested positioning of magnetic poles the magnetic field lines completely penetrate the part of the body to be treated in longitudinal and/or cross-wise direction or a combination of both in a high concentration, whereas in the case of the known arrangement of poles with alternating polarity in pole bands on one surface of the magnetic foil only the upper layers of tissue are influenced by the magnetic field lines.

According to the invention, a greater penetration depth of the magnetic field lines is achieved, particularly from all sides into the body section. Thus, a particularly effective therapeutic effect is brought about. A flux density of 13 mT (130 G) was measured with the foil thickness being 3.0 mm and the inner diameter of the permanent magnetic arrangement according to the invention being 100 mm.

The flux density can be increased according to a further embodiment of the invention when the permanent magnetic arrangement comprises several thin magnetic foils or strips, which are positioned in layers one above the other, whereby a north pole of one foil faces the south pole of the adjacent foil. By this means, one could, for example, double the flux density by doubling the foil thickness without the flexibility being adversely affected. This suggestion is particularly applicable when using cheap permanent magnetic powder.

A simple method of increasing the magnetic foil thickness is to wind the magnetic foil spirally around the part of the body to be treated.

A further increase of the flux density can be brought about by using magnetic foils in which anisotropic magnetic materials have been embedded.

In the case of bone fractures, the invention offers the particular advantage in comparison to the treatment using electromagnetically activated coils, that about the same force line density is reached. This means that the therapeutic effect is also almost as good. The permanent magnetic arrangement according to the invention is, however, of a much simpler design and is cheaper. It costs only about one tenth of the electromagnetic coil appliances currently on the market. Furthermore, it is not connected to electricity mains, so that there is no danger of an electrical shock or too great a warming effect occurring. It can be applied easily by anyone without risk and without previous medical knowledge.

The following embodiments of the invention are explained by the drawings which illustrate as follows:

FIG. 1 an embodiment of the permanent magnetic arrangement in perpendicular longitudinal cross-section in diagrammatic form.

Figure 2:
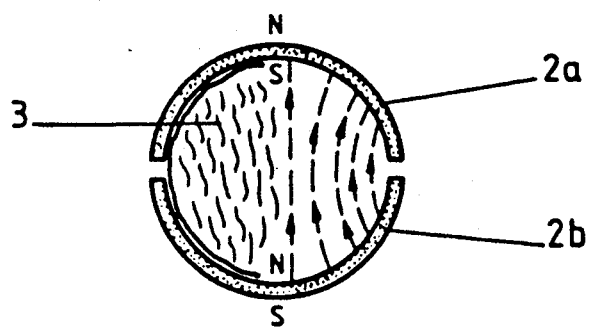

FIG. 2 perpendicular cross-section through the arrangement along the line I—I of FIG. 1.

Figure 3:
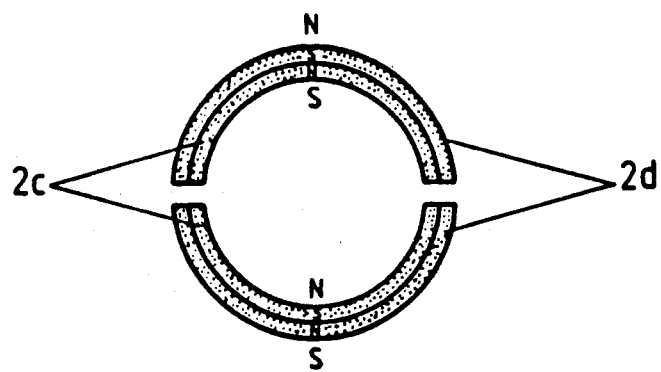

FIG. 3 same cross-section as in FIG. 2, however with two magnetic foils positioned one over the other in layers.

Figure 4:
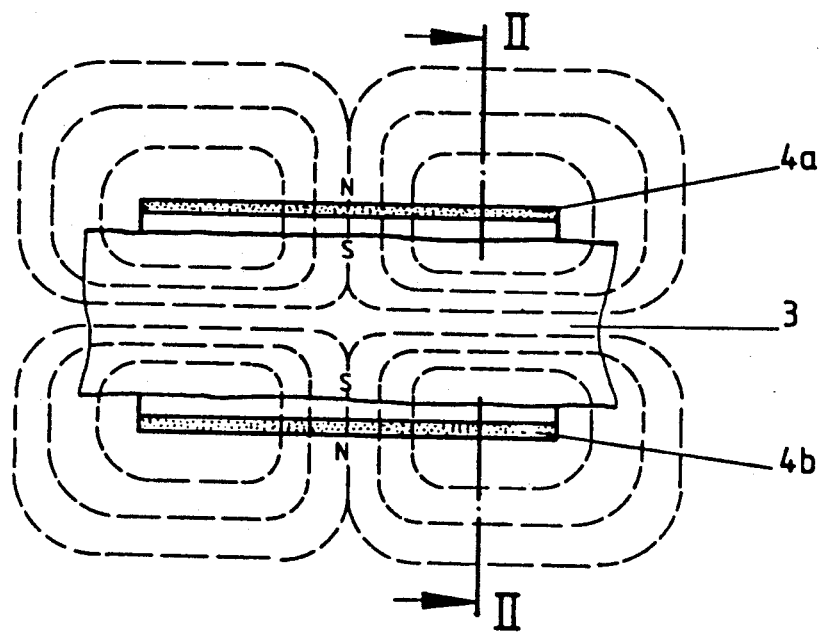

FIG. 4 a different embodiment of the arrangement in perpendicular longitudinal section in diagrammatic form.

Figure 5:
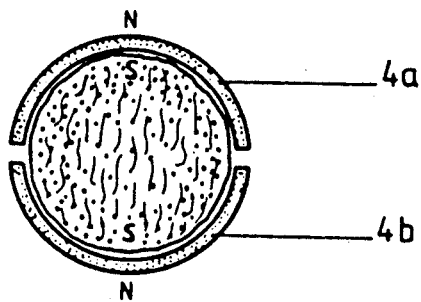

FIG. 5 a perpendicular cross-section through the arrangement along the line II—II of FIG. 4.

Figure 6:
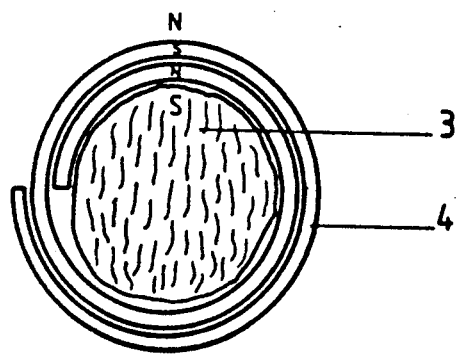

FIG. 6 an embodiment of the arrangement, whereby the magnetic foil is wound spirally around the part of the body to be treated.

Figure 7:
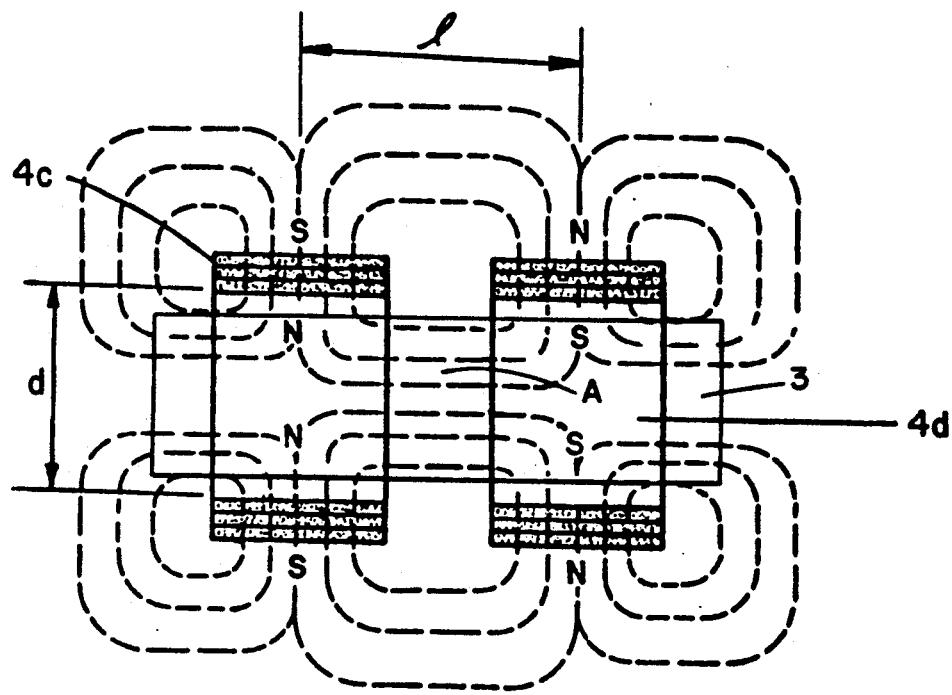

FIG. 7 an embodiment of the arrangement, whereby two tube-shaped magnetic strips are positioned adjacent to but separate from each other.

Figure 8:
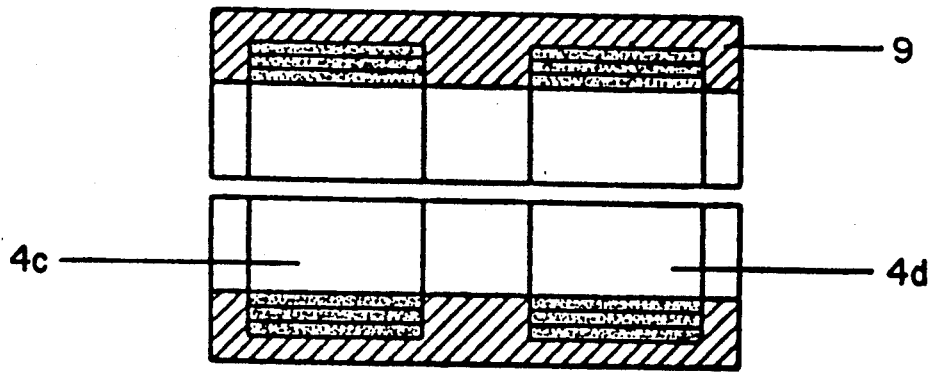

FIG. 8 an embodiment, whereby the separately positioned tube-shaped magnetic strips are fitted in a rigid container.

Figure 9:
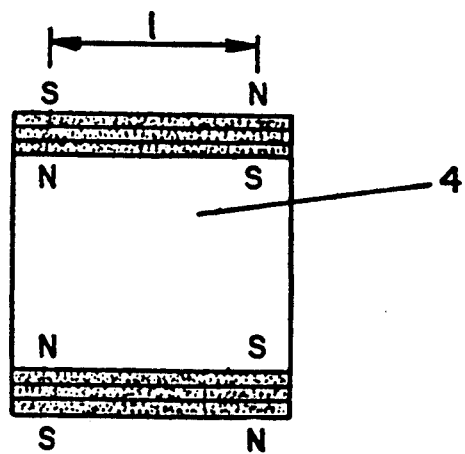

FIG. 9 an embodiment, whereby the multi-layer, tube-shaped magnetic arrangement exhibits an axially opposed magnetization.

Figure 10:
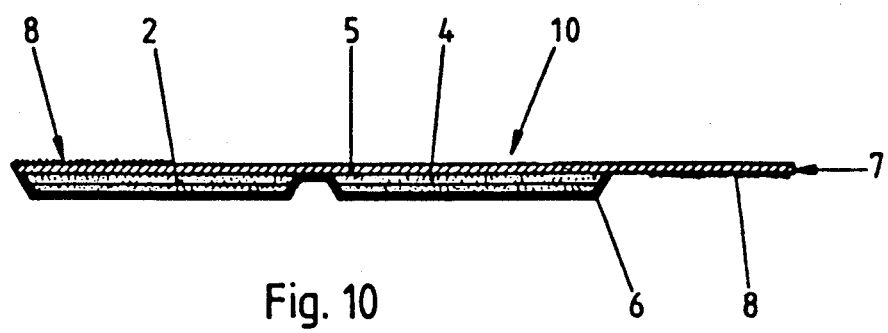
Figure 11:
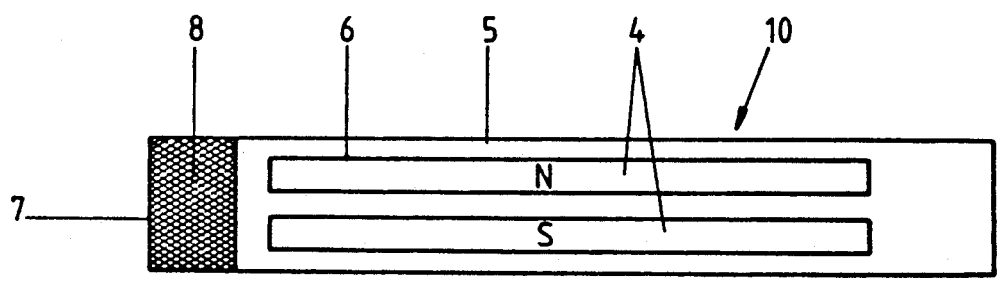

FIGS. 10 and 11 two embodiments, whereby in each case the permanent magnetic arrangement takes the form of a bandage and is shown in perpendicular longitudinal section and from above.

Figure 12:
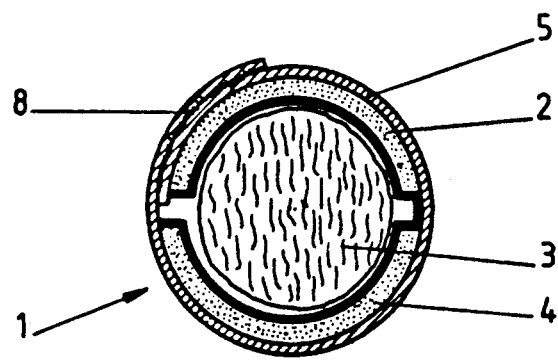

FIG. 12 the magnetic bandage as during the therapeutic application in perpendicular cross-section.

In all embodiments, the permanent magnetic arrangement 1 is made up of one or several flexible magnetic foils. These magnetic foils comprise a rubber-type, flexible, thermoplastic binder, in which highly coercive permanent magnet particles are embedded in fine distribution. The mixture of permanent magnet material and binder is formed on a calendars machine into a foil of the required thickness.

Suitable permanent magnet materials in powder form are particularly: isotropic or anisotropic ferrites on a barium-and/or strontium ferrite base; also lead ferrite or cobalt rare earth alloys and neodyme iron. The latter exhibit a particularly high energy product with very high coercive force and residual magnetization.

The permanent magnetic arrangement 1 according to the invention is shown in diagrammatic form in FIGS. 1-9, in order to illustrate the magnetization, and the path of the magnetic field lines on the body section during application to the part of the body to be treated.

As can be seen in FIG. 1-9, the magnetic foil of the permanent magnetic arrangement 1 is in the shape of a tube during the therapeutic application. In the case of the embodiment according to FIGS. 1 and 2, the magnetic foil comprises two foil pieces 2a and 2b, each of which is in the form of a semi-tube during the therapeutic application. The part of the body to be treated is positioned between the foil pieces. The fastening mechanism is not illustrated in the drawings.

The magnetic foil or foil pieces 2a and 2b exhibit a direction of magnetization running perpendicularly to the foil surface. At the same time, the foil pieces 2a and 2b are positioned in relation to one another in such a manner, that the inner surface of the foil piece 2a faces the part of the body to be treated and has a south pole and the inner surface of the opposite foil piece 2b has a north pole. Due to this particular arrangement, the magnetic field lines cross through the part of the body being treated from the north pole to the south pole, whereby an effective therapeutic action is brought about as a result of the penetration of the magnetic field lines through the part of the body being treated. This Path of the magnetic field lines is illustrated in FIGS. 1 and 2 by dashed lines. The poles are marked by the letters N and S. As one can see from the illustrations, the corresponding counterpoles are positioned on the outer surfaces of the foils or foil pieces.

In FIG. 3, the permanent magnetic arrangement is shown having the same pole arrangement as illustrated in FIGS. 1 and 2. In the case of this embodiment, however, two thin magnetic foil pieces 2c, 2d of equal thickness are positioned one above the other in layers, whereby a north pole of one foil is opposite the south pole of the adjacent foil. The pole sequence is again marked in the drawing by the letters N and S. The advantage of this embodiment is, that the effective field line density is doubled without adversely affecting the flexibility.

In the case of the previously described arrangement with field lines passing cross-wise through the part of the body to be treated, a magnetic field line density of 13 mT (130 G) was measured using an isotropic magnetic foil of 3.0 mm thickness with the diameter of the inner area of the permanent magnetic arrangement roughly corresponding to the diameter of the part of body to be treated.

It lies within the scope of the invention to layer more than two thin foils one over the other. This is particularly necessary when a very high field line density is required because of the large diameter involved (as for application to thigh). This total thickness of the layered arrangement can even reach approximately 10-15 mm. This method of increasing the foil thickness is particularly advantageous when cheaper magnet materials are used, such as isotropic barium ferrite.

A strengthening of the effective field line density is also brought about when anisotropic magnetic foils are used for the magnetic arrangement.

In another embodiment according to FIGS. 4 and 5, the magnetic arrangement 1 comprises two opposing semi-tube-shaped magnetic foil pieces 4a and 4b, which surround the part of body to be treated. Also, here the connecting or fastening mechanisms are not illustrated.

The magnetic foil pieces 4a and 4b produce a direction of magnetization which runs perpendicularly to the foil surface. However, in this case, the semi-tube-shaped foil pieces are positioned in such a manner relative to each other, that on their inner circumferential surfaces facing the part of body to be treated, the south pole is to be found and on the opposite outer surface the counter-pole is to be found, in this case, the north pole. The poles are again marked in the drawing by the letters N and S.

In the case of this embodiment, the magnetic field lines run in a longitudinal or axial direction through the body section 3 positioned inside the tube-shaped magnetic arrangement. The path of the magnetic field lines is shown in FIG. 4 by dashed lines, while the field line density in FIG. 5 is shown by dots.

While in the case of the embodiment according to FIGS. 1-3, a considerable penetration depth or deep action of the magnetic field lines is brought about, in the case of the embodiment according to FIGS. 4 and 5, an effective therapy is possible over a greater length of the part of body to be treated. In an advantageous and simple manner, both methods can be combined.

In the embodiment according to FIG. 6, the magnetic foil 4 of the permanent magnetic arrangement, which exhibits a pole arrangement as described in FIGS. 4 and 5, is wound spirally around the part of body to be treated 3, e.g., a fractured bone. As can be seen in the cross-section illustration according to FIG. 6, the magnetic foil in this case is in two layers, one over the other, so that apart from the simple method of application a simultaneous doubling of the field line density is achieved as previously described. Of course, even a multi-layered arrangement is conceivable.

In the case of this embodiment, it is practical to cover the magnetic foil or strip 4 on the side facing the surface of the skin with a textile fabric.

In the case of the magnetic arrangement according to FIG. 7, two magnetic foils or strips 4c, 4d of tube-shaped design are positioned adjacent to, but separate from, one another during the therapeutic treatment. The tube-shaped magnetic strip 4c has a concentric north pole facing the part of the body 3 to be treated and the other tube-shaped magnetic strip 4d has a concentric south pole facing the part of the body 3 to be treated, as is marked in the drawing by the letters N and S. In this example, three magnetic strips have been layered one over the other in order to increase the thickness of the magnetic strip and the field line density. A relatively good field homogeneity is reached in area A of this embodiment.

According to FIG. 8, the separately, but adjacently, positioned magnetic foils or strips 4c and 4d of tube-shaped design are fitted in a preferably bipartite magnetically permeable housing 9. The hinge and fastening mechanisms are not illustrated.

It is possible, as illustrated in FIG. 9, to magnetize the magnetic foil 4 bipolar with direction of magnetization perpendicular to the foil surface in such a manner, that on the inner perimeter of the tube-shaped structure facing the body section, at least one concentric north pole and at least one concentric south pole are present adjacent to each other but widely apart. The poles are again marked by the letters N and S.

In the case of the permanent magnetic arrangements according to FIGS. 7-9, the middle distance 1 between the concentric poles of varying polarity should be at least as great as the inner diameter d of the tube-shaped magnetic foil 4, which surrounds the part of the body to be treated, in order that a considerable depth action of the magnetic field lines is achieved.

In FIGS. 10 and 11, the permanent magnetic arrangement in the suggested form of a bandage 10 is shown when not in use. According to FIG. 10, two magnetic foil pieces 2, 4 are positioned at a distance from each other in a textile fabric strip 5, e.g., in pockets 6. The magnetic foil pieces can either exhibit a type of magnetization as illustrated in FIGS. 1-3 or 4-7. They could also be positioned in several layers one over the other. The open ends 7 of the textile fabric strip 5 are provided with a Velcro fastener 8. An alternative type of closing mechanism is also conceivable.

In the case of the bandage 10 illustrated in FIG. 11, two magnetic strips 4 have been placed separately but parallel to each other in a textile fabric strip 5, preferably in pockets 6. As can be seen in the drawing, a north pole is to be found on the surface facing the body section of one magnetic strip and on the adjacent magnetic strip a south pole is to be found.

In this arrangement, it is also possible for several magnetic strips to be positioned one over the other and each loose in a pocket and, therefore, displaceable against each other. The open ends 7 of the textile fabric strip 5 are again provided with a Velcro fastener 8.

The bandage illustrated in FIGS. 10 and 11 has been placed around a body section 3, e.g., an arm, according to FIG. 12. One can see the tube-shaped form of the magnetic foil pieces 2, 4, which enclose the body section completely. Corresponding with the magnetic pole arrangements according to the invention, the magnetic field lines penetrate the body section 3 in longitudinal and/or cross-wise direction.

In the case of the bandage 10 illustrated in FIG. 11, the two magnetic strips 4 assume a tube or ring-shape when placed around a body section 3 according to FIG. 12.

The invention is not limited to the embodiments illustrated here. Rather, it is possible to sew the magnetic foil or strips into items of clothing or to wear them over the clothing, e.g., over the stocking on the leg. Due to the great penetration depth of the magnetic field lines, the therapeutic action is still effective in these cases. One could also wear the magnetic arrangement over the plaster cast on a bone fracture in order to speed up the healing process.

I claim:

1. A permanent magnetic arrangement for application to a generally tubular member portion of a human body to direct a magnetic flux field thereinto, said magnetic arrangement comprising two rubber-like flexible magnetic foil strips having high coercive permanent magnetic particles embedded in fine distribution in a thermoplastic binder layer, said strips being of identical tubular form for closely surrounding said portion of said body and positioned axially adjacent to but separate from and in axially spaced relationship to one another, each of said tubular strips having a radially inner surface and a corresponding radially outer surface, said inner surfaces of said two axially spaced tubular magnetic foil strips being formed one as a north magnetic pole and the other as a south magnetic pole and the outer surfaces of said two tubular strips being formed as a magnetic pole of opposite polarity to the corresponding inner surface, all of said poles being of equal strength and oriented only perpendicularly to the longitudinal axis of said tubular forms to thereby create a magnetic field therebetween extending longitudinally of the axis of said tubular forms and spanning the axial spacing between the two tubular strips.

2. A permanent magnetic arrangement according to claim 1, wherein said two axially spaced tubular magnetic foil strips are each constituted by a corresponding plurality of said magnetic foil strips radially layered one on top of another to form a layered assembly thereof, and wherein the surfaces of radially adjacent foil strips which are in contact with each other, are of opposite polarity to each other.

3. A permanent magnetic arrangement according to claim 2, wherein the axial distance between the axial center points of the north and south poles formed on the said inner surfaces of said two tubular magnetic foil assemblies is at least as great as the inner diameter of the tubular shaped magnetic foils.

* * * * *